United States Patent
Allione et al.

(10) Patent No.: US 11,134,837 B2
(45) Date of Patent: Oct. 5, 2021

(54) METHOD FOR DETERMINING AN UPDATED VISUAL CORRECTION NEED FOR DESIGNING A NEW VISION CORRECTING DEVICE

(71) Applicant: Essilor International, Charenton-le-Pont (FR)

(72) Inventors: Pascal Allione, Charenton-le-Pont (FR); Thierry Bonnin, Charenton-le-Pont (FR); Jean Sahler, Charenton-le-Pont (FR); Stéphane Gueu, Charenton le Pont (FR); Sébastien Maurice, Charenton le Pont (FR)

(73) Assignee: Essilor International, Charenton-le-Pont (FR)

( * ) Notice: Subject to any disclaimer, the term of this patent is extended or adjusted under 35 U.S.C. 154(b) by 288 days.

(21) Appl. No.: 16/333,527

(22) PCT Filed: Sep. 14, 2017

(86) PCT No.: PCT/EP2017/073200
§ 371 (c)(1),
(2) Date: Mar. 14, 2019

(87) PCT Pub. No.: WO2018/050780
PCT Pub. Date: Mar. 22, 2018

(65) Prior Publication Data
US 2019/0231185 A1    Aug. 1, 2019

(30) Foreign Application Priority Data

Sep. 15, 2016    (EP) .................................. 16306179

(51) Int. Cl.
*A61B 3/028*    (2006.01)
*A61B 3/00*    (2006.01)
(Continued)

(52) U.S. Cl.
CPC ............ *A61B 3/028* (2013.01); *A61B 3/0025* (2013.01); *A61B 3/10* (2013.01); *G16H 20/00* (2018.01); *G16H 50/50* (2018.01); *G16H 50/70* (2018.01)

(58) Field of Classification Search
CPC ..... A61B 3/04; A61B 3/028; A61B 3/02–3/09
(Continued)

(56) References Cited

U.S. PATENT DOCUMENTS

| 6,386,707 B1 | 5/2002 | Pellicano |
| 9,549,669 B2 | 1/2017 | Limon |

(Continued)

FOREIGN PATENT DOCUMENTS

| CN | 1520270 A | 8/2004 |
| CN | 105163649 A | 12/2015 |
| WO | 2014/195951 A1 | 12/2014 |

OTHER PUBLICATIONS

Marsden, Janet, et al. "How to Measure Distance Visual Acuity." Community Eye Health Journal, 2014 (Year: 2014).*

(Continued)

*Primary Examiner* — Zachary W Wilkes
(74) *Attorney, Agent, or Firm* — Nixon & Vanderhye

(57) ABSTRACT

Disclosed is a method for determining an updated visual correction need for designing a new vision correcting device of an individual already having a previous vision correcting device previously designed to correct his/her vision, wherein, in a first step, a previous level of correction of the previous vision correcting device is acquired, in a second step, a current vision acuity parameter of the individual (Continued)

wearing the previous vision correcting device is assessed, and, in a third step, the updated visual correction need is determined based on the previous level of correction of the previous vision correcting device acquired in the first step and on the current vision acuity parameter assessed in the second step. A complementary visual correction need can also be determined.

10 Claims, 2 Drawing Sheets

(51) Int. Cl.
*A61B 3/10* (2006.01)
*G16H 50/50* (2018.01)
*G16H 50/70* (2018.01)
*G16H 20/00* (2018.01)

(58) Field of Classification Search
USPC .................................................. 351/205, 246
See application file for complete search history.

(56) References Cited

U.S. PATENT DOCUMENTS

| | | | |
|---|---|---|---|
| 9,775,509 B2* | 10/2017 | Fung | G16H 50/70 |
| 2004/0174499 A1 | 9/2004 | Toshima et al. | |
| 2014/0268060 A1 | 9/2014 | Lee et al. | |
| 2017/0079523 A1 | 3/2017 | Limon | |
| 2019/0335993 A1* | 11/2019 | Liang | A61B 3/103 |

OTHER PUBLICATIONS

Meslin, Dominique. Practical Refraction. Essilor Academy Europe, 2008 (Year: 2008).*

Anonymous, "Visual acuity", Wikipedia, 2016, https://en.wikipedia.org/w/index.php?title=Visual_acuity&oldid=679112830, XP055356626, retrieved 2017.

International Search Report and Written Opinion, dated Dec. 18, 2017, from corresponding PCT application No. PCT/EP2017/073200.

Office Action issued in Chinese Patent Application No. 201780057779.2 dated Feb. 1, 2021 with English translation provided.

* cited by examiner

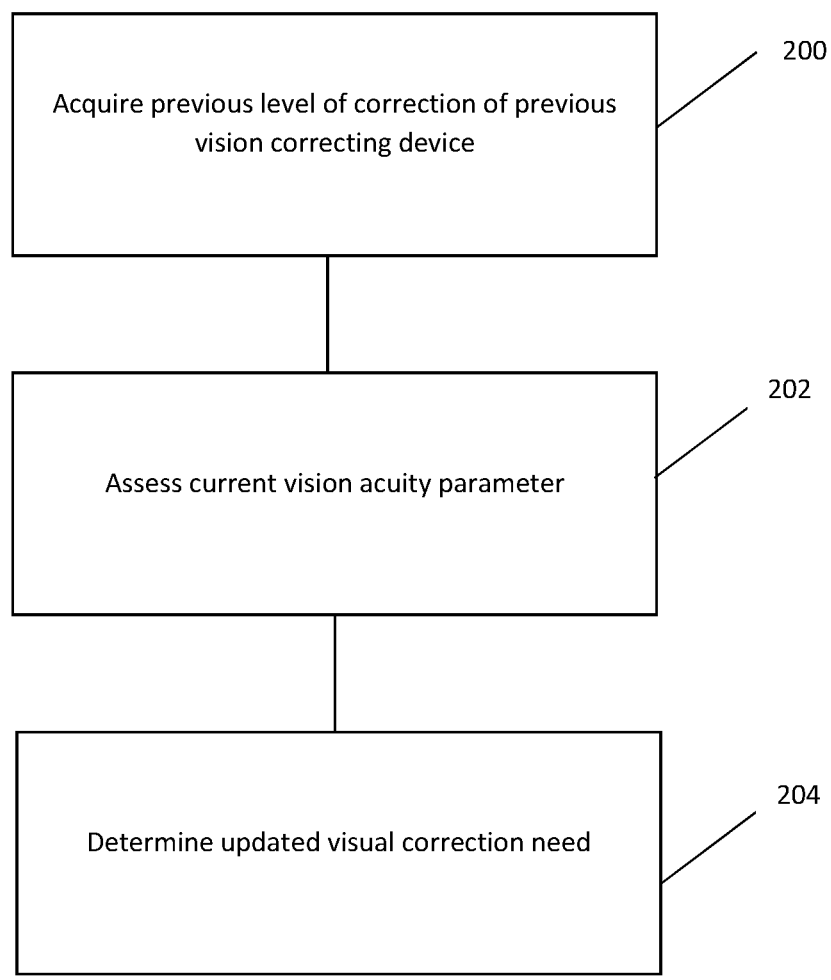

METHOD FOR DETERMINING AN UPDATED VISUAL CORRECTION NEED FOR DESIGNING A NEW VISION CORRECTING DEVICE

TECHNICAL FIELD OF THE INVENTION

The present invention is related to a method for determining an updated visual correction need for designing a new vision correcting device for an individual already having a previous vision correcting device previously designed to correct his/her vision. The method also allows to determine a complementary visual correction need that is to be added to the previous level of correction of the previous vision correcting device for the fabrication of the new vision correcting device. It has applications in the field of optics for the correction of impaired/bad vision of individuals. It can be used for an individual having vision impairment that is already corrected with a pair of glasses or any other equivalent means.

BACKGROUND INFORMATION AND PRIOR ART

Conventionally, the visual correction needed for correcting bad vision is determined by an eye care professional using complex and costly apparatuses.

However, in many instances, notably in countries with few eye care resources, the professionals that may provide correction to people having impaired/bad vision, do not have access to complex and costly apparatuses able to measure the level of needed correction or do not know well the methods used to compute the correction need. This results in people not having proper correction for their vision and thus discomfort and visual fatigue.

There is a method known for measuring the refractive error with a portable phone in WO2014/195951 "SYSTEM AND METHOD FOR MEASUREMENT OF REFRACTIVE ERROR OF AN EYE BASED ON SUBJECTIVE DISTANCE METERING".

A goal of the current invention is to propose another solution to help to the determination of the optical characteristics of a new vision correcting device by determining an updated visual correction need or determining a complementary visual correction need, the previous vision correcting device of the individual having a previous level of correction that is no more sufficient to correct the vision of the individual. In particular, the determination of the updated visual correction need and/or the complementary visual correction need can be implemented using simple tools and still giving accurate results. The method can be adapted to be included in a mobile/portable electronic device, typically a smartphone, and may be used by any person involved in the correction of vision impairments or even the individual needing such a correction. It may be used solely by individuals needing a further correction through the use of a telephone or computer network allowing them to determine their needs and order through the network a pair of glasses with the determined updated visual correction need. The proposed method can easily be used by a candid individual and still providing precise results.

The method proposed here is a new solution to get the visual correction needed for designing a new vision correcting device for an individual without the need of a complex and costly apparatuses and without the mandatory intervention of a professional eye care. It provides accurate solution that can be then used for online ordering of a new vision correcting device for an individual.

SUMMARY OF THE INVENTION

The current invention is related to a method for determining an updated visual correction need for designing a new vision correcting device of an individual already having a previous vision correcting device previously designed to correct his/her vision.

According to the invention, in a first step, a previous level of correction of the previous vision correcting device is acquired, in a second step, a current vision acuity parameter of the individual wearing said previous vision correcting device is assessed, in a third step, said updated visual correction need is determined based on said previous level of correction of the previous vision correcting device acquired in the first step and on said current vision acuity parameter assessed in the second step.

The following characteristics that can be used alone or according to any technical combination are also considered in the context of the invention:

in the third step, a complementary visual correction need is determined based on said current vision acuity parameter assessed in the second step and the complementary visual correction need is added to said previous level of correction of the previous vision correcting device for determining said updated visual correction need, the complementary visual correction need is equal to the updated visual correction need minus the previous level of correction, the updated visual correction need is equal to the previous level of correction plus the complementary visual correction need, the complementary visual correction need is for near vision and/or far vision, the updated visual correction need is for near vision and/or far vision, the individual has two eyes and the method is applied for each of the two eyes of the individual, to determine an updated visual correction need and/or a complementary visual correction need for each eye, the previous vision correcting device was designed according to the content of a prescription that was issued by an eye care professional, said content being a level of correction and the acquisition of the previous level of correction of the previous vision correcting device is done:

by obtaining it from the content of the prescription, or by measuring the correction provided by the individual's previous vision correcting device, the measure of the previous level of correction of the previous vision correcting device is made with a process using a visual target and a mobile device having a camera and in which images of the visual target through the previous vision correcting device are analyzed, the current vision acuity parameter comprises a vision acuity level (first embodiment) and/or a vision acuity distance (second embodiment), the assessment of the current vision acuity parameter of the individual wearing said previous vision correcting device is done through one of the following processes:
  an objective process with a measuring apparatus,
  a subjective process requesting a visual sensorial evaluation from the individual,
  a statistical process,
said updated visual correction need is determined based on the result of a comparison between said current vision acuity parameter of the individual and a predefined vision acuity reference,
said complementary visual correction need is determined based on the result of a comparison between said current vision acuity parameter of the individual and a predefined vision acuity reference,
the predefined vision acuity reference is any value that the eye care professional thinks that is achievable in improving the vision of the individual,
the predefined vision acuity reference is 10/10 or better,
the predefined vision acuity reference is VA_logmar=0 in LogMar units, or better,
the predefined vision acuity reference is 10/10 or better or any other equivalent value in another unit such as for example LogMar,
said updated visual correction need is determined in such a way that the individual obtain, with said new vision correcting device, an updated vision acuity level equal to or higher than said predefined vision acuity reference,
said updated visual correction need and said previous level of correction of the previous vision correcting device each comprises an optical power,
said updated visual correction need comprises a Sphere optical power, $P_{Sphere}$, related to the correction of nearsightedness or farsightedness, and a Cylinder optical power, $P_{Cylinder}$, related to the correction of astigmatism, and wherein said complementary visual correction need comprises a Sphere complementary optical power, $P_{CSphere}$, related to the correction of nearsightedness or farsightedness, and a Cylinder complementary optical power, $P_{CCylinder}$, related to the correction of astigmatism,
in the updated and complementary visual corrections, the correction for Cylinder includes the axis of the cylinder,
according to a first embodiment, the current vision acuity parameter comprises a vision acuity level,
the predefined vision acuity reference is a desirable level of vision acuity to obtain with a new vision correcting device providing the updated visual correction need,
the desirable level of vision acuity is greater than the current vision acuity level,
if the current vision acuity level of the individual is equal to or greater than the predefined vision acuity reference, then the third step is not executed,
if the current vision acuity level of the individual is lower than the predefined vision acuity reference, then the third step is executed,
the current vision acuity level comprises a current spherical acuity level, $Acuity_{Sphere}$, that is related to the nearsightedness or farsightedness of the individual and a current cylindrical acuity level, $Acuity_{Cylinder}$, that is related to the astigmatism of the individual
in the third step, the determination of the complementary visual correction need is based on a function that gives a relation between the current vision acuity level, the updated visual correction need and a Best Corrected Visual Acuity, BCVA, and wherein the Best Corrected Visual Acuity, BCVA, is the predefined vision acuity reference,
the function is based on the fact that, for an individual having the current vision acuity level, if the updated visual correction need is given to him or her, the individual will then have the predefined vision acuity reference,
the function is based on a Swaine law,
the Swaine law related to the correction of nearsightedness or farsightedness is $Acuity_{Sphere}=\text{Max}(-\text{Log}(0.25/P_{Sphere}), BCVA)$, where BCVA is the predefined vision acuity reference,
the Swaine law related to the correction of astigmatism is $Acuity_{Cylinder}=\text{Max}(-\text{Log}(2^{1/2} \quad 0.25/P_{Cylinder}), BCVA)$, where BCVA is the predefined vision acuity reference,
in the third step, the Sphere complementary optical power is computed according to $P_{Sphere}=0.25/\exp(-Acuity_{Sphere})$ where $Acuity_{Sphere}$ is expressed in LogMar units,
in the third step, the Cylinder complementary optical power is computed according to $P_{Cylinder}=2^{1/2} \ 0.25/\exp(-Acuity_{Cylinder})$ where $Acuity_{Sphere}$ is expressed in LogMar units,
in the first embodiment, where the current vision acuity parameter is a current vision acuity level, the assessment of the current vision acuity level of the individual wearing said previous vision correcting device is done through a statistical process in which it is assumed:
  that when the previous vision correcting device was made at the related previous age of the individual, the correction of vision provided at that time gave the individual the predefined vision acuity reference, and that the evolution of the vision acuity level of the individual along his/her ages follows statistical curves or laws based on the evolutions of acuities in a population of individuals along their ages, and
  wherein the current age of the individual is obtained and the previous age of the individual is determined and
  wherein the current vision acuity level is obtained from the curve or law passing at the predefined vision acuity reference at the previous age, the current vision acuity level being the point at the current age of said passing curve or law,
the previous age of the individual is determined by asking him,
the previous age of the individual is determined from the date the previous vision correcting device was made,
the statistical assessment of the current vision acuity level of the individual wearing said previous vision correcting device is done through a statistical process in which vision acuity parameters are deduced from visual badness/impairment parameters and the reverse,
the statistical assessment of the current vision acuity level if for a current spherical acuity level, $Acuity_{Sphere}$, that is related to the nearsightedness or farsightedness of the individual,
the statistical assessment of the current vision acuity level if for a current cylindrical acuity level, $Acuity_{Cylinder}$, that is related to the astigmatism of the individual,
according to a second embodiment of the invention, the assessment of the current vision acuity parameter of the individual wearing said previous vision correcting device is done through a subjective process in which series of optotypes are shown to the individual, and the current vision acuity parameter of the individual wearing said previous vision correcting device is performed through a subjective process in which at least one optotype is shown to the individual, wherein said current vision acuity parameter comprises a current vision acuity distance assessed in the second step as an optimal value of the distance defined
  between the eyes of the individual and said previous vision correcting device or between said previous vision connecting device and the at least one optotype,
this optimal distance value being suitable for obtaining a desired acuity levelupon the visual sensorial evaluation of the individual.

The invention is also related to a system for the execution of a method for determining an updated visual correction need for designing a new vision correcting device of an individual already having a previous vision correcting device previously designed to correct his/her vision, wherein said system comprises a portable electronic device comprising at least an image acquisition module, a display screen and a computer program executed in the electronic device, said computer program being configured to operate the electronic device for the execution of at least a part or full of one or more steps of the method of the invention.

The following embodiments that can be used alone or according to any technical combination are also considered in the context of the invention:
the portable electronic device further comprises an input interface,
the system is configured to measure distances between a face of an individual and the portable electronic device, said measurements being obtained from images from the image acquisition module,
the portable electronic device is connected to a remote server or computer via a network, said remote server or computer being programmed to execute at least a part or full of one or more steps of the method of the invention,
the portable electronic device is an electronic device comprising at least a display screen, an input interface and a mapping sensor, said mapping sensor being able to measure distances between a face of an individual and the portable electronic device,
the mapping sensor is selected from an ultrasonic sensor capable of measuring distances, an optical sensor capable of measuring distances, a moiré optical sensor capable of measuring distances, a scanning light beam sensor capable of measuring distances, a 3D camera capable of measuring distances,
the portable electronic device is designed to ensure that the display screen displays the at least one predetermined symbol used for vision tests,
the portable electronic device is connected through a network to an external computer or server,
the portable electronic device is a smartphone or a tablet or a portable computer.

The invention is also related to a program adapted to perform the method of the invention when installed and executed in the system, and more particularly in the electronic device, of the invention, The invention is also related to a program adapted to perform the method of the invention when installed and executed in the system, and more particularly in the remote server or computer of the invention.

BRIEF DESCRIPTION OF THE DRAWINGS

FIG. 2 is a flow chart illustrating operations according to one or more exemplary embodiments of the present invention.

DETAILED DESCRIPTION OF EXAMPLE(S)

Figure 1A:
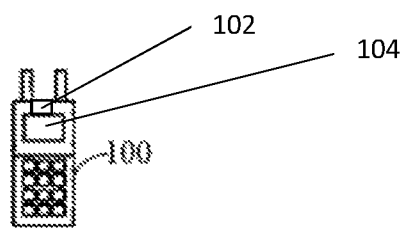
FIGS. 1A and 1B is a frontal view and a schematic view of a mobile communications device according to one or more exemplary embodiments of the present invention.

The following description will allow a good understanding of how the invention may be implemented.

In its general principle, the invention is related to a method for determining an updated visual correction need (global correction for a new vision correcting device) or a complementary visual correction need (the correction to be added to the previous level of correction of the previous vision correcting device) for an individual already having a previous vision correcting device but that is no more sufficient to correct his/her visual deficiencies.

Generally, the Visual Acuity is a measure of the visual power of an individual. It is usually determined by one's ability to read letters of various sizes of a test chart at a standard distance from the eyes. The normal sight/vision is 20/20 but it can be expressed in other units. Most of the time it is expressed with a unit that is a fraction but other units may be used, for example in LogMar unit, a LogMar=0 is equivalent to 20/20.

The vision impairment/badness may concern the far vision and/or the near vision of each eye of the individual. Moreover, the vision impairment may be different in the radial direction of the vision axis in case of astigmatism. This is for that reason that the acuity and also the correction are expressed for a Sphere referential and for a Cylinder referential. The Sphere referential is related to the nearsightedness (myopia) or farsightedness (hyperopia) characteristics of the vision of the individual. The Cylinder referential is related to astigmatism for which an angle for the correction is also determined when the acuity is assessed.

The main purpose of the invention is to allow the automatic, preferably online, determination of a new vision correcting device for an individual who already has a previous vision correcting device, which previous level of correction can be acquired, and using an assessment, preferably by the measurement of the current vision acuity parameter of the individual wearing said previous vision correcting device or a statistical model of the evolution in time of the vision acuity level of a population to which the individual is supposed to pertain.

In its main aspect, the proposed method of the invention is executed in three steps, illustrated in FIG. 2:

In a first step (200), a previous level of correction given by the previous vision correcting device is acquired.

Then, in a second step (202), a current vision acuity parameter of the individual wearing said previous vision correcting device is assessed either directly with a measurement or indirectly from a statistical model of the evolution of vision acuity.

Finally, in a third step (204), it is determined an evolution of the degradation of the vision and more particularly, the determination of an updated visual correction need or of a complementary visual correction need to complete/add to the previous level of correction. The updated visual correction need or the complementary visual correction need is determined based on the previous level of correction of the first step and on the current vision acuity parameter of the second step.

Typically, an individual having a previous vision correcting device that was made some years ago and that corrected his/her vision at that time is now no more adequate and the individual seeks a new vision correcting device able to correct him/her now. This is due to the fact that the vision acuity of the individual degraded along years as he/she ages. Such degradation is well known and is statistically defined with curves or law giving a model of relation between the ages and for example the level of visual defect or the acuity level or even the needed correction level.

The second step is used for two main purposes: to assess the current vision acuity level that will be used in the third step and, also, to check that a new vision correcting device will be able to correct the individual now. Indeed, if the individual wearing his/her previous vision correcting device has a current vision acuity level that is currently acceptable or at its best, the new vision correcting device will be of no use in terms of correction. Of course, if the individual desire is to get a new vision correcting device for another reason, nothing prohibits that.

In the first step, the acquisition of the previous level of correction may be done directly using the prescription given to the individual by the eye care professional or more generally by the person who made the previous vision correcting device.

Figure 1B:
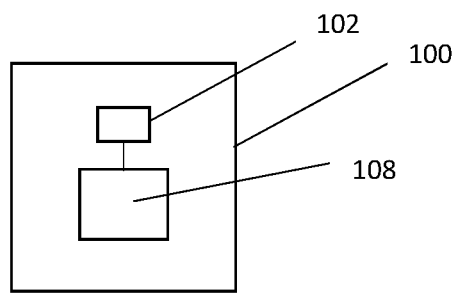

The previous level of correction may be instead measured on the previous vision correcting device using a dedicated measuring apparatus. The measurement can instead be done using a process involving a mobile device 100 having a camera 102 and a visual target, illustrated in FIGS. 1A and 1B. Such process is the preferred solution because it can be done easily at a very low cost. In addition, it can be executed by the individual in case the method of the invention is executed to get/purchase a new vision correcting device through a communication network and notably INTERNET.

For example, it can be used a process determining a parameter of an optical equipment, notably a vision correcting device, and which comprises:
  an optical equipment positioning step, during which an optical equipment comprising a pair of optical lenses mounted on a spectacle frame is positioned in a first position,
  a portable electronic device positioning step, during which a portable electronic device (mobile device) 100 comprising an image acquisition module 108 is positioned in a second position determined and/or known relatively to the first position so as to acquire an image of a distant element seen through at least part of the optical lenses of the optical equipment in the first position,
  a parameter determining step, during which at least one optical parameter of the optical equipment is determined based on the image of a distant element seen through at least part of the optical lenses of the optical equipment in the first position.

Instead, it can be used a process for determining a parameter of an optical device comprising at least an optical lens, the method comprising:
an optical system providing step, during which an optical system comprising a visual target, the optical device and an image acquisition module is provided in an initial configuration state,
a parameter determining step during which a parameter of the optical device is determined based on the blur level of the images of the visual target acquired by the image acquisition module through the optical device in at least two different configuration states.

Note that this acquisition in the first step can be done separately for each eye and/or for near vision and far vision. More generally, the previous level of correction is acquired for the Cylinder and Sphere referentials. Practically, the acquired previous levels of corrections are associated to their relative eye and referential and in case of astigmatism, the reference axis is also part of the previous level of correction.

As a general principle, all the processes, steps, elements discussed in the current invention are preferably considered as individual methods or elements for each eye and for each type of vision defect, in Cylinder and Sphere referentials, for the far and near visions. In other words, the updated and/or complementary visual correction needs are determined for each eye and for both referentials.

For the second step, the current vision acuity parameter of the individual wearing his/her previous vision correcting device is assessed.

According to an advantageous embodiment, the current vision acuity parameter comprises a vision acuity level.

The assessed current vision acuity parameter is compared to a fixed threshold called predefined vision acuity reference that is in relation to a good or to a best level of vision acuity. For example, the predefined vision acuity reference can be set to 10/10 or to VA_logmar=0 according to the units that are chosen. This comparison is done because, if the current vision acuity level of the individual is already equal to or even greater than the predefined vision acuity reference, there is no need to provide a new vision correcting device on vision correction/improvement reasons. Indeed, with a good or best current vision acuity level there is no or few possibilities to improve vision acuity and if a new vision correcting device has to be made, the same correction as the previous level of correction can be used.

If this is not the case and that there is a possibility to improve visual acuity, the third step is executed.

Preferably, in the second step, it is first made a check to verify that an improvement of the vision acuity can be expected with a new vision correcting device. A solution is to use a portable/mobile device 100 like a computer or tablet or a smartphone and on which screen 104 is displayed a visual test. The individual is asked to wear his/her current eyewear (this is the previous vision correcting device), to look at a visual test displayed on the screen of the mobile device 100. The visual test used may be basic acuity test, having 10/10 or higher acuity line. The visual test is preferably done monocularly to determine the current vision acuity level for each eye. For that, the individual is instructed to hide one of his/her eyes.

Such visual test can be conducted at distance above 2 m, or above 4 m, meaning that this test is done in far vision, and that the current vision acuity level assessed is for far vision correction.

Such visual test can also be done for near vision, typically 40 cm. In this case, if the individual wears a progressive lens in his/her previous vision correcting device, it will be tested if the previous ADDITION (that is the correction for near vision) is already enough in relation to the corresponding predefined vision acuity reference. If the individual wears single vision lenses, it will be tested if he needs an ADDITION in relation to the corresponding predefined vision acuity reference.

For near vision tests, the distance from the individual and the test can be determined using a camera of the portable or mobile device and a known size object, such as credit card or a scaled rule. For determining the distance for the far vision, the individual is instructed to count a number of footsteps between him and the mobile device.

If monocular visual acuity is not correct, less than 10/10 for instance or less than 8/10 mm for at least one eye, it is assumed that this comes from a degradation of the visual acuity of the individual, meaning that it is possible to improve vision acuity.

In order to confirm that situation, it is proposed the following process:
  when using far vision test, the individual is instructed to get closer to the visual test, 1 m for instance, and the visual acuity is checked again. If the visual acuity increases, it means that the correction of the previous vision correcting device that is on the face of the individual is the cause and that improvement can be expected.

when using near vision test, the individual is instructed to get further from the initial 40 cm to 60 cm for instance, and if the visual acuity increases, it means that the correction of the previous vision correcting device that is on the face of the individual is the cause and that improvement can be expected.

Preferably, when the distance between the individual and the visual test on the mobile device is increasing or reducing, the size of the visual test is modified so that its angular size is the same for the individual whatever the distance between the individual and the visual test.

Note that this step may also be achieved using a questionnaire asking to the individual if he is satisfied with his previous vision correcting device or not, for instance if he has difficulties to read road signs, to read books . . . .

If the individual is not satisfied and/or has difficulties in reading, then this means that an improvement can be expected with a new vision correcting device.

For all the solutions requesting measurement of the visual acuity of the individual or a visual feed-back from the individual, the individual is wearing his/her previous vision correcting device.

The following solutions may be used to determine the updated and/or complementary visual correction needs in the third step:

first solution using Swaine's law model and applying it the current vision acuity level assessed through measurement, second solution with modifications and measurements of parameters allowing to have an acuity at least equal to the predefined vision acuity reference, third solution with the use of a questionnaire.

For the two first solutions, in order to assess the visual acuity of the individual, it is possible to use the display screen of the mobile device as the support of optotypes of visual tests allowing to measure the current vision acuity level.

For the first solution, to assess the visual acuity, the individual must be placed at a fixed known distance of the screen of the mobile device on which it is shown him a set of optotypes (letters, Parent's quadrant, horizontal and vertical fringes, . . . ). A regular protocol is then used to assess his/her acuity. This assessment may be done for the two eyes separately or in a binocular mode.

Then to determine the complementary visual correction needs (it is reminded that the individual is wearing his/her previous vision correcting device during the assessment of his/her current visual acuity level), a computation based on the Swaine's law that links acuity to the needed correction, is used.

This Swaine's law for the visions according to Sphere and Cylinder referentials and applied to the invention is:

$$\text{Acuity}_{Sphere}=\text{Max}(-\text{Log}(0.25/P_{CSphere}), \text{BCVA})$$

$$\text{Acuity}_{Cylinder}=\text{Max}(-\text{Log}(2^{1/2}\ 0.25/P_{CCylinder}), \text{BCVA}$$

where $P_{CSphere}$ and $P_{CCylinder}$ are the complementary corrections, BCVA (Best corrected visual acuity) is the predefined vision acuity reference. The BCVA, and thus the predefined vision acuity reference, may be assumed to be 10/10 or VA_logmar=0 in LogMar.

As a general principle, the updated corrections are expressed as a Sphere optical power, $P_{Sphere}$, related to the correction of nearsightedness or farsightedness, and a Cylinder optical power, $P_{Cylinder}$, related to the correction of astigmatism. Those corrections are correcting respectively a sphere defect and a cylinder defect in the vision of the individual. Note that due to the fact that the individual is wearing his/her previous vision correcting device during the assessment of acuity for Sphere and Cylinder, this is the complementary optical power $P_C$ that are determined and that is why $P_{CSphere}$ and $P_{CCylinder}$ are used in the application of the Swaine's law to the current invention.

It is then possible to determine the correction for Sphere and Cylinder with only two acuity assessments for each eye. In addition, the axis for Cylinder correction may be measured using Parent's quadrant during the assessment of the current visual acuity level.

Again, as the individual is wearing his/her previous vision correcting device, the $P_{CSphere}$ and $P_{CCylinder}$ in the law are corrections that concern the residual sphere and cylinder to add to the previous levels of correction to get the updated visual correction needs.

Thus, knowing the loss of acuity and the type of residual defect of vision, if it is related to sphere or to cylinder, it is possible to calculate the value of the residual correction $P_{CSphere}$ or $P_{CCylinder}$. For instance, $P_{CSphere}=0.25/\exp(-\text{VA\_logmar})$ for sphere.

Here, the $P_{CSphere}$ sign is depending on the sign of $P_{Sphere}$ and in case of myopia where $P_{Sphere}$ is negative the complementary power should be negative and in case of hyperopia this is the reverse.

To determine if the defect of vision is residual sphere or cylinder, it is possible to conduct a test using parent test having lines oriented at different directions (0°-180°, step of 30° or less). If the individual see all lines with same sharpness, then the residual defect of vision is sphere. Otherwise, residual defect is cylinder or a combination of cylinder and sphere defects. The sharpest line of the Parent test will give cylinder axis orientation.

When cylinder defect or combination of cylinder and sphere defects exist, it is possible to propose to the individual a visual test having orientations similar and orthogonal to the cylinder axis. These tests may be Gabor pattern (fringes test), having varying spatial frequency to test acuity for similar or orthogonal directions.

A test may consist into three Gabor patterns having same spatial frequency, with orientations slightly varying (−15°, 0°, +15°) and the individual is asked to give the orientation of best perception. If the individual do not perceive correctly the patterns, spatial frequency is reduced and the process is done again.

The spatial frequency gives a visual acuity, VA_0, for the direction 0°

Then same can be done for 90° giving VA_90.

An empiric law is the used to determine the relation between VA_0, VA_90 and the residuals for Sphere and Cylinder referentials:

$$S=F(VA\_0+VA\_90), C=G(VA\_0-VA\_90)$$

The function F and G are deduced from previous formulae $\text{Acuity}_{Sphere}$ and $\text{Acuity}_{Cylinder}$.

For the second solution, the process is to change one parameter of the optical system formed by the eye, the lens of the previous vision correcting device and the image of the visual test in order to have an acuity at least equal to the predefined vision acuity reference. This can be done for each eye separately or for both eyes.

Two possibilities are allowable for such a process.

The first possibility is to change the distance between the eye and the lens of the previous vision correcting device, the individual staying at a constant distance from the visual test.

The second possibility is to change the distance between the lens and the visual test, the individual wearing his/her previous vision correcting device without moving it.

Preferably, the visual test is displayed on a screen of a mobile device. Still preferably, the mobile device is a portable electronic device comprising at least an image acquisition module, a display screen and a computer program configured to operate the portable electronic device for the execution of at least a part or full of one or more operational steps of the method of the invention.

For the first possibility, the myopic individual may take his glasses (previous vision correcting device) away from his/her eyes until his acuity reaches the predefined vision acuity reference. In practice, the best way is to put the glasses far from the eyes in such a way that the individual has the maximum of acuity and then to approach them as long as the acuity do not fall. When the acuity starts to fall, this defines a limit distance of the lens to the eyes. Supposing that the corresponding limit distance of the lens to the eyes is that way obtained and that the regular distance of the lens to the eyes when the glasses are correctly situated on the nose of the individual is also known, it is possible to calculate the related corrective focal length and then to calculate the power to add to the previous level of correction by adding the corrective focal length.

Different types of optotypes are useable to cover acuity assessment related to the sphere and other related to the cylinder/astigmatism to determine the additional sphere/power and cylinder correction to add to the previous level of correction of the previous vision correcting device of the individual to correct him precisely. Again, this can be also done for each eye.

For instance, if the individual has $PP_{Sphere}$ correction for the previous vision correcting device and d is the distance variation between the two positions (i.e. between the limit distance and the regular distance), then the updated visual correction need for sphere $P_{Sphere}$ is given by the following relation: $1/P_{Sphere}=1/PP_{Sphere}+d$ (d>0).

So, it is possible to add to the individual extra positive power to check if he has hyperopic residual defect. Note: This residual defect may come from refraction evolution, or may come from an inaccurate refraction.

The variation of the eye-lens distance may be measured for example using images of the face of the individual taken by the camera of the mobile device displaying the visual test, such measure being made for the two positions (i.e. limit distance and regular distance) of the glasses and using the following relation:

$$(D+d)/D=(G+g)/G$$

where D is the regular distance, D+d is the limit distance, G is the size, from the image, of the frame at distance D and G+g is the size, from the image, of the frame at distance D+d. Of course it is assumed that the frame holding the glasses of the previous vision correcting device is a rigid structure.

The third solution is based on a statistical process in which it is supposed that the individual visual parameters follows, as his/her ages, the ones of a population that has been assessed/surveyed for said visual parameters.

With this third solution, the easy way is to ask to the individual, using an online questionnaire for example, his age and the date when his bought his previous vision correcting device. With this information and for certain ametropies it is possible to predict his/her new correction using mean evolution curves of such ametropies with the ages.

For example, curves of the predicted progression of myopia knowing it at the age of 9 for boys and girls are available.

The mean evolution curves of myopic eye are thus known and this allows to predict the variation of power (negative lens) to add to the lens of the previous vision correcting device to well correct the individual.

The same can be done for presbyopia as curves of the evolution of the amplitude of accommodation (that is directly linked to the ADDITION for a presbyopic individual) are also available. It is thus possible to predict the variation of the ADDITION to correct the vision of an individual, knowing his previous ADDITION/previous level of correction and the age when it was given with his/her previous vision correcting device. Note that this process may be improved if more than one point along the curve is obtained: if multiple previous corrections or acuity levels for multiple previous ages of the individual are available.

In the given example given so far, a mobile device which has a program to execute processes needed in the method of the invention is used notably to assess the visual acuity and possibly distances and also to determine the updated visual correction need or the complementary visual correction need. It should be understood that in case the mobile device has communication means for exchanging data with an external, possibly remote, computer or server, for example through TCP/IP or telephone network, part of the program can be executed in the computer or server. For example, images of the face of the individual can be sent to a remote computer for computing distance and/or the final computation of the updated visual correction need or the complementary visual correction need. This could be useful because the external computer or server has greater computing capabilities than the portable device that is a mobile/portable device and, also, because the external computer can have access to additional data that can be used, for example previous correction for the individual and statistical information related to the vision of a population to which the individual is supposed to pertain.

The invention claimed is:

1. A method for determining an updated visual correction need for designing a new vision correcting device of an individual already having a previous vision correcting device previously designed to correct vision of the individual, the method comprising:

acquiring a previous level of correction of the previous vision correcting device;

assessing a current vision acuity parameter of the individual wearing said previous vision correcting device, the current vision acuity parameter comprising a current vision acuity level assessed through a statistical process comprising:

determining a previous age of the individual when the previous vision correcting device was made, obtaining a predefined vision acuity reference for the individual of a correction of vision for the individual when the previous vision correcting device was made at the previous age of the individual, obtaining a current age of the individual, obtaining a plurality of statistical curves or laws based on evolutions of acuities in a population of individuals along ages of the individuals, an evolution of vision acuity levels of the individual along ages of the individual following the statistical curves or laws, and obtaining the current vision acuity level of the individual from a statistical curve or a law of the statistical curves or laws passing at the predefined vision acuity reference at the determined previous age, the current vision acuity level being a point at the current age of the individual of the passing curve or the law; and determining said updated visual correction need based on said acquired previous level of correction of the previous vision correcting device and said assessed current vision acuity parameter.

2. The method according to claim 1, wherein the determining of the updated visual correction need comprises determining a complementary visual correction need based on said assessed current vision acuity parameter, and adding the complementary visual correction need to said previous level of correction of the previous vision correcting device to determine said updated visual correction need.

3. The method according to claim 2, wherein said updated visual correction need and said previous level of correction of the previous vision correcting device each comprise an optical power.

4. The method according to claim 3, wherein said updated visual correction need comprises a Sphere optical power ($P_{Sphere}$) related to a correction of nearsightedness or farsightedness, and a Cylinder optical power ($P_{Cylinder}$) related to a correction of astigmatism, and wherein said complementary visual correction need comprises a Sphere complementary optical power related to the correction of nearsightedness or farsightedness, and a Cylinder complementary optical power related to the correction of astigmatism.

5. The method according to claim 4, wherein, in the determining the updated visual correction need, the Sphere complementary optical power is computed according to $P_{Sphere}=0.25/\exp(-Acuity_{Sphere})$ where $Acuity_{Sphere}$ is expressed in LogMar units, and the Cylinder complementary optical power is computed according to $PCylinder=2^{1/2}\ 0.25/\exp(-Acuity_{Cylinder})$ where $Acuity_{Sphere}$ is expressed in LogMar units.

6. The method according to claim 2, wherein the current vision acuity level comprises a current spherical acuity level ($Acuity_{Sphere}$) that is related to a nearsightedness or farsightedness of the individual and a current cylindrical acuity level ($Acuity_{Cylinder}$) that is related to an astigmatism of the individual, and the determining of the complementary visual correction need is based on a function that gives a relation between the current vision acuity level, the updated visual correction need and a Best Corrected Visual Acuity, the Best Corrected Visual Acuity being the predefined vision acuity reference.

7. The method according to claim 1, wherein, the previous vision correcting device was designed according to the content of a prescription that was issued by an eye care professional, said content being a level of correction, and the previous level of correction of the previous vision correcting device is acquired by one of:

(i) obtaining the previous level of correction from the content of the prescription, and (ii) measuring a correction provided by the previous vision correcting device of the individual.

8. The method according to claim 7, wherein the previous level of correction of the previous vision correcting device is measured with a process using a visual target and a mobile device having a camera and in which images of the visual target through the previous vision correcting device are analyzed.

9. A non-transitory computer-readable medium on which is stored a program adapted to perform the method of claim 1 when installed and executed in a computer system to execute a method for determining an updated visual correction need to design a new vision correcting device of an individual already having a previous vision correcting device previously designed to correct vision of the individual, wherein said computer system comprises a portable electronic device comprising one or more processors configured to acquire an image and a display screen.

10. A system comprising:

a portable electronic device comprising one or more processors configured to acquire an image;

a display screen; and a computer program executed in the electronic device, said computer program being configured to operate the electronic device to execute a method for determining an updated visual correction need for designing a new vision correcting device of an individual already having a previous vision correcting device previously designed to correct vision of the individual by acquiring a previous level of correction of the previous vision correcting device;

assessing a current vision acuity parameter of the individual wearing said previous vision correcting device, the current vision acuity parameter comprising a current vision acuity level assessed through a statistical process comprising:

determining a previous age of the individual when the previous vision correcting device was made, obtaining a predefined vision acuity reference for the individual of a correction of vision for the individual when the previous vision correcting device was made at the previous age of the individual, obtaining a current age of the individual, obtaining a plurality of statistical curves or laws based on evolutions of acuities in a population of individuals along ages of the individuals, an evolution of vision acuity levels of the individual along ages of the individual following the statistical curves or laws, and obtaining the current vision acuity level of the individual from a statistical curve or a law of the statistical curves or laws passing at the predefined vision acuity reference at the determined previous age, the current vision acuity level being a point at the current age of the individual of the passing curve or the law; and determining said updated visual correction need based on said acquired previous level of correction of the previous vision correcting device and said assessed current vision acuity parameter.

* * * * *